United States Patent

Putz et al.

[11] Patent Number: 6,004,262
[45] Date of Patent: Dec. 21, 1999

[54] VISUALLY-POSITIONED ELECTRICAL MONITORING APPARATUS

[75] Inventors: David A. Putz, Franksville; David K. Dunn, Elm Grove, both of Wis.

[73] Assignee: Ad-Tech Medical Instrument Corp., Racine, Wis.

[21] Appl. No.: 09/072,125

[22] Filed: May 4, 1998

[51] Int. Cl.[6] .............................. A61B 1/22; A61B 17/36; A61N 1/00
[52] U.S. Cl. .......................... 600/114; 600/104; 600/129; 600/373; 600/377; 600/393; 606/41; 606/46; 607/116; 607/117
[58] Field of Search .................................. 600/104, 114, 600/129, 345, 373, 377, 380, 393; 606/41, 46; 607/116, 117, 119, 129, 133

[56] References Cited

U.S. PATENT DOCUMENTS

| | | | |
|---|---|---|---|
| 4,782,819 | 11/1988 | Adair | 600/109 |
| 4,850,359 | 7/1989 | Putz | 128/642 |
| 5,064,424 | 11/1991 | Bitrolf | 606/46 |
| 5,080,660 | 1/1992 | Buelna | 606/45 |
| 5,215,103 | 6/1993 | Desai | 128/784 |
| 5,293,868 | 3/1994 | Nardella | 128/642 |
| 5,325,845 | 7/1994 | Adair | 600/393 |
| 5,405,375 | 4/1995 | Ayers et al. | 600/114 |
| 5,458,606 | 10/1995 | Cohen et al. | 606/108 |
| 5,462,544 | 10/1995 | Saksena et al. | 600/373 |
| 5,484,435 | 1/1996 | Fleenor et al. | 606/46 |
| 5,486,173 | 1/1996 | Vancaillie | 606/45 |
| 5,545,200 | 8/1996 | West et al. | 607/122 |
| 5,555,618 | 9/1996 | Winkler | 600/393 |
| 5,674,184 | 10/1997 | Hassler, Jr. | 600/176 |
| 5,849,028 | 12/1998 | Chen | 606/41 |
| 5,882,346 | 3/1999 | Pomeranz et al. | 604/525 |

Primary Examiner—Linda C. M. Dvorak
Assistant Examiner—Brad C. Blaise
Attorney, Agent, or Firm—Jansson, Shupe, Bridge & Munger

[57] ABSTRACT

A visually-positioned electrical monitoring apparatus includes an electrical assembly comprising an elongate, flaccid dielectric body having at least one electrical contact, a passage and an open distal end. An endoscope extends through the passage and has its distal end substantially in registry with the distal end of the body. A method for placing an electrical monitoring assembly to coact with human tissue at a target site includes providing the aforedescribed monitoring assembly, extending an endoscope into the passage, aligning the distal end of the endoscope with the distal end of the body and visually guiding the assembly to the site.

15 Claims, 3 Drawing Sheets

VISUALLY-POSITIONED ELECTRICAL MONITORING APPARATUS

FIELD OF THE INVENTION

This invention is related generally to surgery and, more particularly, to surgical devices for electrical applications involving inserting the device into human tissue.

BACKGROUND OF THE INVENTION

Many types of surgical procedures involve insertion of some type of device into human tissue. For example, U.S. Pat. No. 5,674,184 (Hassler, Jr.) describes, in general terms, endoscopic surgery within body cavities, organs and joints. The patent is directed to a surgical cutting tool or trocar having a cannula for inserting an obdurator into tissue to be cut. The obdurator has a chisel-shaped, solid, optically-clear tip and guidance of the tip is by an endoscope. The tip has side-by-side electrodes (used for tissue cutting) connected to wires brought out via grooves in the outer wall of the tube.

U.S. Pat. No. 5,458,606 (Cohen et al.) generally describes a procedure for relieving hydrocephalus, otherwise known as water on the brain. The disclosed neuro endoscope is inserted into the cranial cavity. Such endoscope uses a stainless steel hollow tube (a "hypotube" as the patent calls it) containing an illuminating fiber bundle, a central image fiber and irrigating and vacuum channels. The bundle, fibers and channels are secured near the tube distal end by epoxy filler and insertion of the endoscope is through a catheter.

U.S. Pat. No. 4,850,359 (Putz) discloses what has come to be known as a depth electrode for monitoring electrical activity in the brain. Electrode placement to a depth in the brain is by using X-ray, magnetic resonance imaging (MRI) or the like.

A paper titled "Intraoperative Neurophysiology of the Corticospinal Tract" by V. Deletis and K. Kothbauer, published by Institute of Neurology and Neurosurgery, Beth Israel Medical Center North Division, New York, N.Y. mentions using electrodes for transcranial electrical stimulation and for recording D-waves from the spinal epidural or subdural space. The paper describes where and how electrodes are inserted and is incorporated herein by reference.

A feature of the trocar disclosed in the Hassler, Jr. patent is that it is rigid. The neuro endoscope disclosed in the Cohen et al. patent is also apparently rigid since it uses a stainless steel tube. While rigidity is undoubtedly needed in a surgical cutting tool or neuro endoscope of the described types, rigidity is a disadvantage in a device which must be temporarily implanted at a very-hard-to-reach site in the human body. And neither the Hassler, Jr. trocar nor the Cohen et al. endoscope is described as being suitable for electrical monitoring or stimulation.

An electrical monitoring apparatus which may be visually positioned and which is suitably small and flexible for use in very-hard-to-reach body sites would be an important advance in the art.

OBJECTS OF THE INVENTION

It is an object of this invention to provide an electrical monitoring apparatus overcoming some of the problems and shortcomings of devices of the prior art.

Another object of this invention is to provide an electrical monitoring apparatus which is flexible and capable of being visually positioned.

Yet another object of this invention is to provide a method for visually placing an electrical monitoring assembly to coact with human tissue at a target site. How these and other objects are accomplished will become apparent from the following descriptions and from the drawings.

SUMMARY OF THE INVENTION

Aspects of the invention involve a visually-positioned electrical monitoring apparatus which includes an electrical assembly with an elongate, cylindrical, flaccid body made of dielectric material. The body has at least one electrical contact around its outside surface and, most preferably, several such contacts which may be made of platinum or the like. The body has a lumen or passage through it which terminates in an open distal end. In a highly preferred embodiment, the passage is the sole passage in the body. An endoscope extends through the passage and has its distal end substantially in registry with the distal end of the body.

More specifically, the concentric passage is defined by a body wall and the distal end of the endoscope terminates in a distal section having an exterior surface around it. This surface and the body wall contact one another when the distal end of the endoscope is substantially in registry with the distal end of the body.

In other aspects of the invention, the body has an exterior surface, a proximal end spaced from the body distal end and an opening located between the body proximal and distal ends. The opening, which might be termed a side wall opening, extends between the passage and the exterior surface. An electrical wire extends from the inner surface of the contact, through a tiny hole in the dielectric body and along the passage toward and through the opening.

A first passage section is between the distal end of the body and the opening and has the endoscope and the wire in it. A second passage section is between the opening and the proximal end of the body and has only the endoscope in it. To put it in other words, the wire extends from the contact through the opening in the body and the endoscope extends from the distal end of the body through the body proximal end.

In yet other aspects of the invention, the endoscope includes a stop surface abutting the body at the body proximal end. The endoscope includes a gripping hub and in one embodiment, the stop surface is on the hub. In another embodiment, the endoscope includes a slidable abutment member frictionally mounted on it. The stop surface is on the abutment member.

Yet other aspects of the invention involve a method for placing an electrical monitoring assembly to coact with human tissue at a target site. The method includes providing an electrical monitoring assembly comprising an elongate, flaccid body having at least one electrical contact therearound, a passage therethrough and an open distal end. An endoscope having a distal end is extended into the passage. The distal end of the endoscope is substantially aligned with the distal end of the body. When the endoscope and the body are relatively positioned in that way, the assembly is visually guided to the site to be monitored or stimulated.

In a specific assembly, an electrical wire extends from the contact along the passage. The extending step includes sliding the endoscope along the wire. In a more specific version of the method, the extending step includes inserting the distal end of the endoscope into the proximal end of the body and sliding the 'scope along the wire.

After the assembly is guided to the site, the guiding step is followed, in either order, by the steps of withdrawing the endoscope from the body and connecting the wire to an electrical apparatus for monitoring electrical activity at the site. For a specific procedure, the site is in the spinal column and the guiding step includes visually guiding the assembly to the epidural space of the spinal column. For another specific procedure, the guiding step includes visually guiding the assembly to the subarachnoid space of the spinal column.

Other details of the invention are set forth in the following detailed description and in the drawings.

DETAILED DESCRIPTIONS OF THE PREFERRED EMBODIMENTS

Figure 1:
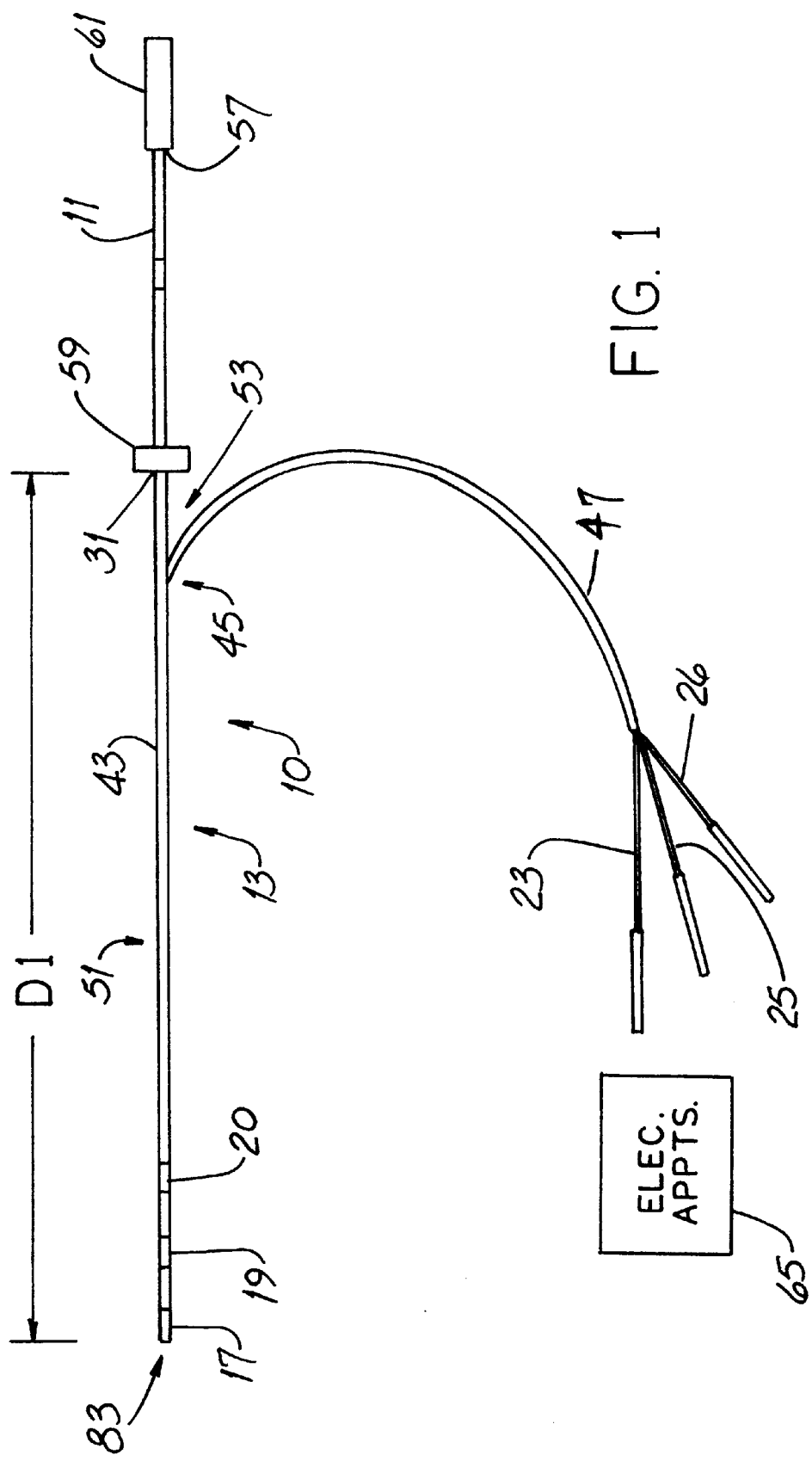
FIG. 1 is a side elevation view of the new apparatus shown in conjunction with an electrical apparatus.

Referring first to FIGS. 1, 2, 3 and 4, the visually-positioned electrical monitoring apparatus 10 includes an endoscope 11 within an electrical assembly 13. The assembly 13 has a small-diameter, elongate, cylindrical, flaccid body 15 made of flexible dielectric (i.e., electrically insulating) material. A silicone material or a polyurethane material are among the suitable materials.

The body 15 has at least one, and preferable several, collar-like, tubular electrical contacts 17, 19 closely fitted around its outside surface 21. Each contact 17, 19 is permanently attached to a separate insulated wire 23, 25, respectively, which extends from the contact 17, 19 through a tiny opening 27 in the body 15 and along the concentric passage 29 toward the body proximal end 31.

The passage 29 terminates in an open distal end 33. And in a highly preferred embodiment, the passage 29 is the sole passage in the body 15. The endoscope 11 extends through the passage 29 and when the apparatus 10 is ready for visual positioning in human tissue, the distal end 35 of the endoscope 11 is substantially in registry with the distal end 33 of the body 15.

Figure 3:
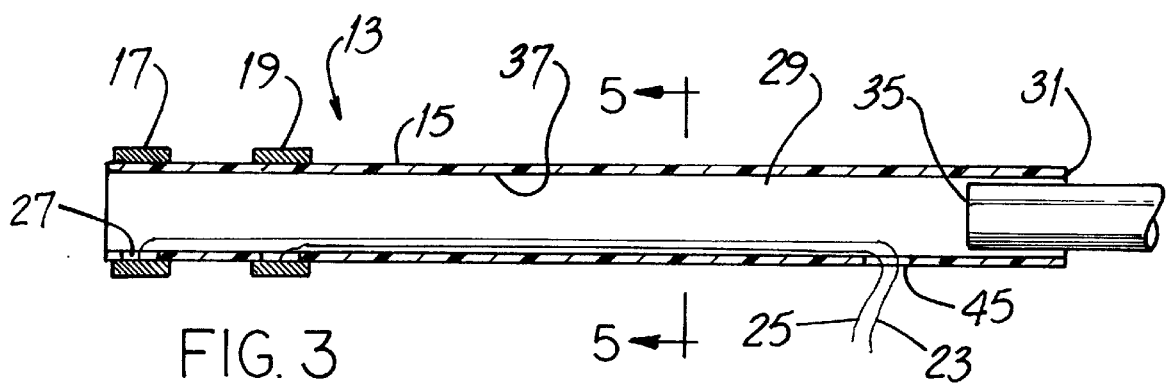
FIG. 3 is a section view, greatly enlarged, of portions of the apparatus. Parts are broken away and shown in full representation.
Figure 4:
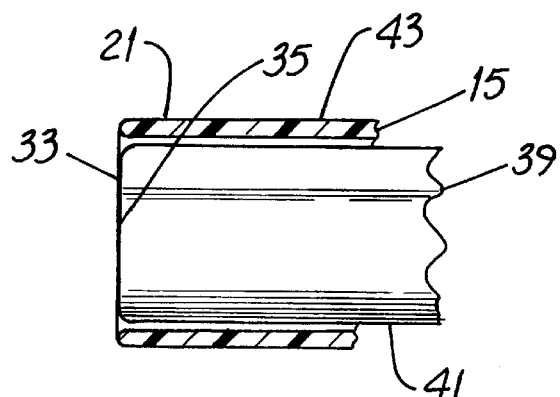
FIG. 4 is a section view, even more greatly enlarged, of portions of the apparatus. Parts are broken away and shown in full representation.

Referring particularly to FIGS. 3 and 4, the concentric passage 29 is defined by a body wall 37 and the distal end 35 of the endoscope 11 terminates a distal section 39 having an exterior surface 41 around it. This surface 41 and the body wall 37 contact one another when the distal end 35 of the endoscope 11 is substantially in registry with the distal end 33 of the body 15.

Referring now to FIGS. 1 and 3, the body 15 has an exterior surface 43, the proximal end 31 spaced from the body distal end 33 and a wire exit opening 45 located between the body proximal and distal ends 31, 33, respectively. The opening 45, which might be termed a side wall opening, extends between the passage 29 and the exterior surface 43. The electrical wires 23, 25 from the contacts 17, 19 extend from the inner surface of a respective contact 17, 19, through a respective tiny opening 27 in the dielectric body 15 and along the passage 29 toward and through the opening 45. In a specific embodiment, the wires 23, 25, 26 may be surrounded by a "bundling" protective sheath 47 after such wires 23, 25 exit the opening 45. (FIG. 1 shows three contacts 17, 19 and 20 and three wires 23, 25, 26 while FIG. 3 shows two contacts 17, 19 and two wires 23, 25 to illustrate the fact that the number of contacts and wires may vary, depending upon the application for the apparatus 10.)

A first passage section 51 is between the distal end 33 of the body 15 and the opening 45 and has the endoscope 11 and the wire(s) 23, 25 in it. A second passage section 53 is between the opening 45 and the proximal end 31 of the body 15 and has only the endoscope 11 in it. To put it in other words, when the apparatus 10 is ready for placement, the wires 23, 25 extend from the contacts 17, 19 through the opening 45 in the body 15 and the endoscope 11 extends from the distal end 33 of the body 15 to and through the body proximal end 31.

Figure 2:
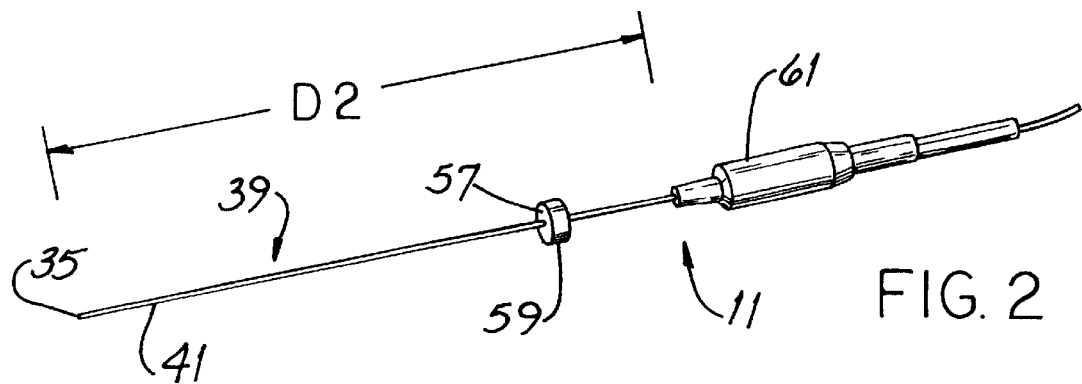
FIG. 2 is a perspective view of an endoscope equipped with a slidable abutment member.

Referring particularly to FIGS. 1 through 5, the endoscope 11 includes a stop surface 57 which abuts the body 15 at the body proximal end 31. In one embodiment, the endoscope 11 includes a slidable abutment member 59 frictionally mounted on it and the stop surface 57 is on the abutment member 59. The endoscope 11 includes a 5 gripping hub 61 and in another embodiment, the stop surface 57 is on the hub 61. An advantage of the embodiment shown in FIG. 2 is that, for endoscopes 11 of varying length, the abutment member 59 may be positionally adjusted to accommodate the body 15, irrespective (within limits) of the length of such body 15. That is, the abutment member 59 may be adjusted to hold the distal end 35 of the endoscope 11 substantially in registry with the distal end 33 of the body 15 while the apparatus 10 is being placed.

Other aspects of the invention involve a method which includes providing the electrical monitoring assembly 13 as described above. The endoscope 11 is extended into the passage 29 by inserting the 'scope distal end 35 into the proximal end 31 of the body 15 and hence along the passage 29 until the distal end 35 of the endoscope 11 is substantially aligned with the distal end 33 of the body 15. This arrangement is highly preferred since most endoscopes 11 have a "seeing eye," e.g., a fiber optic strand exposed at the distal end 35. The resulting visual image is displayed on a screen not unlike a TV screen.

If the endoscope 11 is fitted with an abutment member 59, such member 59 is moved to abut the proximal end 31 of the body 15 while retaining the ends 33, 35 in substantial alignment. If the endoscope 11 and body 15 are cooperatively configured so that the dimension D1 of the body 15 and the dimension D2 of the endoscope 11 are substantially equal, the endoscope 11 is extended into the passage 29 until the stop surface 57 on the hub 61 35 contacts the proximal end 31 of the body 15. When the endoscope 11 and the body 15 are relatively positioned so that the distal end 35 of the endoscope 11 is substantially aligned with the distal end 33 of the body 15, the apparatus 10 is visually guided to the site to be monitored or stimulated.

Figure 5:
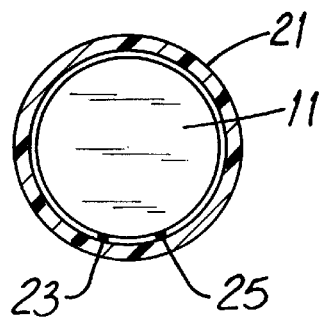
FIG. 5 is a view, in full section, of the body of the electrical assembly taken along the viewing plane 5—5 of FIG. 3 and with the endscope shown in the body passage. The electrical contacts of the assembly are omitted.

In a specific assembly 13, the extending step includes sliding the endoscope 11 along the wires 23, 25 as indicated in FIGS. 3 and 5. In a more specific version of the method, the extending step includes inserting the distal end 35 of the endoscope 11 into the proximal end 31 of the body 15 and sliding the 'scope 11 along the wires 23, 25. After the assembly 13 is guided to the site, the guiding step is followed, in either order, by the steps of withdrawing the endoscope 11 from the body 15 and connecting the wire(s) 23, 25, 26 to an electrical apparatus 65 for monitoring electrical activity at the site or for electrically stimulating tissue at the site.

Figure 6:
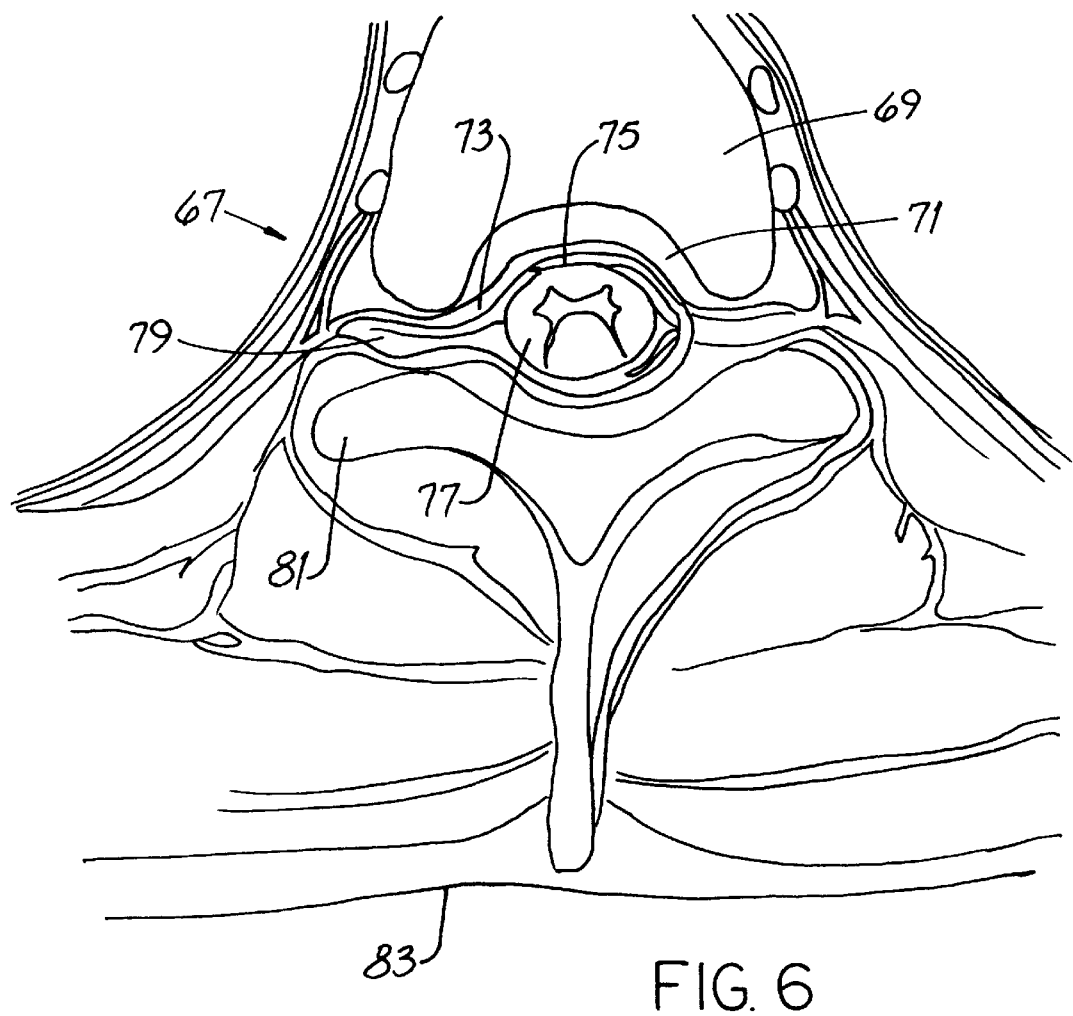
FIG. 6 is a representative, downwardly looking section view of the human spine.

Referring also to FIG. 6, yet other aspects of the invention involve a method for placing an electrical monitoring assembly 13 to coact with human tissue at a target site in the spine 67 of a human patient. The spine 67 includes, toward the front of the patient, the vertebral body 69. It also includes the epidural space 71, the dura mater 73, the subarachnoid space 75, the spinal cord 77, the spinal ganglion 79 and the lamina 81. For further orientation of the viewer of FIG. 6, the exposed skin of the patient's back is at 83.

For a specific procedure, the site is in the spinel 67 and the guiding step includes visually guiding the assembly 13 to the epidural space 71. For another specific procedure, the guiding step includes visually guiding the assembly 13 to the subarachnoid space 75.

While the principles of this invention have been described in connection with specific embodiments, it should be understood clearly that these descriptions are made only by way of example and are not intended to limit the scope of the invention. It is also to be understood that while the apparatus 10 including its assembly 13 are often placed generally vertically in the epidural space 71 or the subarachnoid space 75, they may be placed laterally. And the apparatus 10 is also suitable for use in monitoring and/or stimulating other human tissue, e.g., brain tissue.

What is claimed:

1. A visually-positioned electrical monitoring apparatus including:
    an electrical assembly comprising an elongate, flaccid dielectric body having at least one electrical contact therearound, a passage therethrough and an open distal end; and
    an endoscope extending through the passage and having its distal end substantially in registry with the distal end of the body.

2. The apparatus of claim 1 wherein:
    the passage is defined by a body wall;
    the distal end of the endoscope terminates in a distal section having an exterior surface extending therearound; and
    the exterior surface and the body wall contact one another when the distal end of the endoscope is substantially in registry with the distal end of the body.

3. The apparatus of claim 2 wherein:
    the body is generally cylindrical;
    the passage is concentric in the body; and
    the passage is the sole passage in the body.

4. The apparatus of claim 1 wherein the body includes:
    a proximal end spaced from the body distal end;
    an exterior surface; and
    an opening located between the body proximal and distal ends and extending between the passage and the exterior surface.

5. The apparatus of claim 4 wherein:
    an electrical wire extends from the contact along the passage;
    a first passage section is between the distal end of the body and the opening and has the endoscope and the wire therein; and
    a second passage section is between the opening and the proximal end of the body and has only the endoscope therein.

6. The apparatus of claim 5 wherein:
    the wire extends from the contact through the opening; and
    the endoscope extends from the distal end of the body to the proximal end of the body.

7. The apparatus of claim 1 wherein:
    the body has a proximal end and a distal end; and
    the endoscope includes a stop surface abutting the body at the proximal end.

8. The apparatus of claim 7 wherein the endoscope includes a gripping hub and the stop surface is on the hub.

9. The apparatus of claim 7 wherein the endoscope includes an abutment member frictionally mounted thereon and the stop surface is on the abutment member.

10. A method for placing an electrical monitoring assembly to coact with human tissue at a target site and including the steps of:
    providing an electrical monitoring assembly comprising an elongate, flaccid body having at least one electrical contact therearound, a passage therethrough and an open distal end;
    extending into the passage an endoscope having a distal end;
    substantially aligning the distal end of the endoscope with the distal end of the body; and
    visually guiding the assembly to the site.

11. The method of claim 10 wherein:
    an electrical wire extends from the contact along the passage; and wherein:
    the extending step includes sliding the endoscope along the wire.

12. The method of claim 11 wherein the body includes a proximal end spaced from the body distal end, and wherein:
    the extending step includes inserting the distal end of the endoscope into the proximal end of the body.

13. The method of claim 10 wherein the guiding step is followed, in either order, by the steps of:
    withdrawing the endoscope from the body; and
    connecting the wire to an electrical apparatus for monitoring electrical activity at the site.

14. The method of claim 10 wherein the site is in the spinal column and the guiding step includes visually guiding the assembly to the epidural space of the spinal column.

15. The method of claim 10 wherein the site is in the spinal column and the guiding step includes visually guiding the assembly to the subarachnoid space of the spinal column.

* * * * *

UNITED STATES PATENT AND TRADEMARK OFFICE
CERTIFICATE OF CORRECTION

PATENT NO. : 6,004,262

DATED : December 21, 1999

INVENTOR(S) : David A. Putz et al and David K. Dunn

It is certified that error appears in the above-identified patent and that said Letters Patent is hereby corrected as shown below:

Col. 4, line 27, replace "a 5 gripping" with --a gripping--;
Col 4, line 42, replace "hence" with --thence--;
Col. 4, line 56, replace "61 35 contacts" with --61 contacts--.

Signed and Sealed this

Eighth Day of August, 2000

Attest:

Q. TODD DICKINSON

Attesting Officer

Director of Patents and Trademarks